United States Patent
Bragd et al.

(10) Patent No.: US 6,936,710 B2
(45) Date of Patent: Aug. 30, 2005

(54) PROCESS FOR OXIDIZING PRIMARY ALCOHOLS

(75) Inventors: Petter Bragd, Göteborg (SE); Arie Cornelis Besemer, Amerongen (NL)

(73) Assignee: SCA Hygiene Products Zeist B.V., Zeist (NL)

( * ) Notice: Subject to any disclaimer, the term of this patent is extended or adjusted under 35 U.S.C. 154(b) by 13 days.

(21) Appl. No.: 10/013,654

(22) Filed: Dec. 13, 2001

(65) Prior Publication Data

US 2002/0072600 A1 Jun. 13, 2002

Related U.S. Application Data

(60) Provisional application No. 60/255,899, filed on Dec. 18, 2000.

(30) Foreign Application Priority Data

Dec. 13, 2000 (EP) .............................. 00204483

(51) Int. Cl.[7] .......................... C07G 17/00; C07H 1/00; C07H 3/00; C08B 37/00
(52) U.S. Cl. ..................... 536/124; 536/18.5; 536/18.6; 536/18.7; 536/45; 536/56; 536/63; 536/102; 536/105; 536/123; 536/123.1
(58) Field of Search .............................. 536/18.5, 18.6, 536/18.7, 45, 56, 63, 102, 105, 123, 124, 123.1, 1.11, 4.1

(56) References Cited

U.S. PATENT DOCUMENTS 6,310,200 B1 * 10/2001 Vermaas ..................... 536/124

FOREIGN PATENT DOCUMENTS

| EP | 1 086 938 | 3/2001 |
|----|-----------|--------|
| WO | 95/07303 | 3/1995 |
| WO | 96/38484 | 12/1996 |
| WO | 99/57158 | 11/1999 |
| WO | 01/00681 | 1/2001 |

OTHER PUBLICATIONS

Bolm C., et al.,"Catalytic Synthesis of Aldehydes and Ketones Under Mild Conditions Using TEMPO/Oxone", *Org. Lett. ACS,* (Published on Web) 2(8) 1173–1175, 2000.
Brik, M. E., "Oxidation of Secondary Amines to Nitroxides with Oxone in Aqueous Buffered Solution", *Tetrahedon Lett.,* (Elsevier Science LTD) 36 (31):5519:5522, 1995.
Davis, N. J. and Flitsch, S. L., "Selective Oxidation of Monosaccharide Derivatives to Uronic Acids", *Tetrahedron Lett.* (Pergamon Press Ltd) 34(7): 1181–1184, 1993.
Kochkar, H., et al., "Regioselective Oxidation of Hydroxyl Groups of Sugar and its Derivatives Using Silver Catalysts Mediated by TEMPO and Peroxodisulfate in Water", *J. Catalysis,* (American Press) 194(2): 343–351, 2000.

* cited by examiner

*Primary Examiner*—James O. Wilson
*Assistant Examiner*—Patrick T. Lewis
(74) *Attorney, Agent, or Firm*—Burns, Doane, Swecker & Mathis, L.L.P.

(57) ABSTRACT

Primary hydroxyl groups in a substrate having both primary and secondary hydroxyl groups can be selectively oxidized to carbaldehyde and/or carboxyl groups by contacting the substrate with a cyclic nitroxyl compound in the presence of a peroxosulfate as a co-oxidant and by carrying out the reaction at a temperature below 30° C. and at a pH below 9. The process is halogen-free and metal-free and is especially suitable for oxidizing polysaccharides.

13 Claims, No Drawings

PROCESS FOR OXIDIZING PRIMARY ALCOHOLS

This application claims priority under 35 U.S.C. §§ 119 and/or 365 to 00204483.2 filed in Europe on 13 Dec. 2000 and U.S. Provisional Application No. 60/255,899 filed on 18 Dec. 2000; the entire content of which is hereby incorporated by reference.

FIELD OF THE INVENTION

The invention relates to the selective oxidation of primary alcohols, using an oxidizing agent in the presence of a catalytic amount of a di-tertiary-alkyl nitroxyl compound, especially 2,2,6,6-tetramethylpiperidin-1-oxyl (TEMPO).

BACKGROUND ART

Such a process is known from *Tetrahedron Lett.* 34, 1181–1184 (1993), which describes the oxidation of monosaccharides wherein the non-primary hydroxyl groups are partly protected, using sodium hypochlorite, potassium bromide and TEMPO in a two-phase solvent system (dichloromethane and water) to produce the corresponding uronic acid. WO 95/07303 describes a process for oxidizing carbohydrates with hypochlorite and TEMPO, using a pH of 9–13 in an aqueous median. The oxidation of carboxymethyl and hydroxyethyl derivatives of starch and cellulose and other starch ethers with TEMPO is described in WO 96/38484.

These prior art oxidations have the advantage of being selective, in that oxidation of primary alcohol groups is strongly favored over oxidation of secondary alcohol groups. However, the known processes use hypochlorite as the actual oxidizing agent and thus produce chloride and some chlorinated byproducts: for complete oxidation of primary alcohols to carboxylic acids, two molar equivalents of hypochlorite are used and two molar equivalents of chloride are produced. WO 99/57158 describes the oxidation of carbohydrates using TEMPO and peracetic acid in the presence of bromine.

Recently, Kochkar et el. (*J. Catalysis* 194, 343–351 (2000)) described the TEMPO-mediated oxidation of α-methyl-D-glucoside (α-MDG), 1,2-propanediol, saccharose and starch with ammonium peroxodisulfate in the presence of a supported sliver catalyst in water at pH 9.5 at 25° C. The oxidation of α-MDG and propanediol was successful (78% conversion and 99% selectivity for oxidation of primary hydroxyl group for α-MDG, 90% conversion and 75% selectivity for propanediol), but the oxidation of saccharose was mediocre (20% conversion) and oxidation of starch was unsuccessful (less than 1% conversion). In the absence of the silver catalyst, the TEMPO oxidation of α-MDG with peroxodisulfate was poor (9% conversion), while replacing peroxodisulfate by Oxone® ($2KHSO_5.KHSO_4.K_2SO_4$) in the presence of silver resulted in only 6% conversion. Thus the teaching of this prior art is that the utility of persulfates for oxidizing primary alcohols is restricted to small substrate molecules and practically to the use of ammonium peroxodisulfate, and that the assistance of a silver catalyst is mandatory. The oxidation of benzyl alcohol and other alcohols with TEMPO and Oxone® in organic solvent to produce aldehydes end ketones was described by Bolm et al. (*Org. Lett* 2. 1173–1175 (2000)).

BRIEF DESCRIPTION OF THE INVENTION

It was found now that the TEMPO-mediated selective oxidation of primary alcohol functions can be carried out without using equivalent amounts of chlorine compounds and with high conversion rates, using a peroxosulfate as a co-oxidant. The process of the invention is characterized by being performed under mild conditions (pH below 9 and temperature below 30° C.), in the substantial absence of a metal catalyst. When carried out on polysaccharides, the reaction proceeds with little, if any, depolymerization. The pH is preferably between 6 and 9, most preferably between 6.5 and 8.5, and the temperature is preferably below 25° C., most preferably below 15° C. It is preferred that the peroxosulfate is added carefully, in order to avoid local side-reactions.

DETAILED DESCRIPTION OF THE INVENTION

In the following description, reference is made to TEMPO only for the sake of simplicity, but it should be understood that other cyclic and/or di-tert-alkyl nitroxyls, such as 4,4-dimethyloxazolidine-N-oxyl (Doxyl), 2,2,5,5-tetramethylpyrrolidine-N-oxyl (Proxyl) and 4-hydroxy-TEMPO and derivatives thereof, especially 4-acetamido TEMPO, and those described in WO 95/07303 can be substituted for TEMPO. The catalytic amount of nitroxyl is preferably 0.1–10%, more preferably 0.2–3% by weight, based on the primary alcohol, or 0.1–10 mol % (0.2–3%) with respect to the primary alcohol.

The peroxosulfate present in the process of the invention serves for regenerating TEMPO. The peroxosulfate may be a straight peroxomonosulfate, $MHSO_5$, $M_2SO_5$ or the persulfuric acid $H_2SO_5$, wherein M is an alkali metal or other metal (taking account of its valency in the formula), ammonium or substituted ammonium. Most preferably, the peroxosulfate is Oxone® ($2KHSO_5.KHSO_4.K_2SO_4$), which is commercially available. It is not necessary and not recommended to use any halogen, as a co-oxidant. The amount of peroxosulfate is equivalent to the amount of primary hydroxyl groups to be oxidized. If complete oxidation of —$CH_2OH$ groups to carboxyl groups —COOH is desired, 2–2.4 moles of peroxosulfate per mol of primary hydroxyl groups is advantageously used.

The process of the invention results in oxidation of primary alcohols initially to the corresponding aldehydes, and eventually to the corresponding carboxylic acids. In general, the second oxidation step, from aldehyde to carboxylic acid, proceeds at a faster rate than the first step, i.e. the oxidation from alcohol to aldehyde. Under usual experimental conditions, the maximum fraction of aldehyde functions present will be below about 10 (based on the number of primary hydroxyls available for oxidation). The present process is especially favorable for the selective oxidation of primary hydroxyl groups in alcohols having a secondary alcohol function in addition to the primary alcohol, such as 1,6-octanediol, 1,9-octadecanediol, sugar alcohols, glycosides, and in particular carbohydrates having primary alcohol functions, especially polysaccharides having chain lengths of at least 5 anhydroglycose units, such as glucans (starch, cellulose), furanofructans, galactans, (galacto) mannans, and the like. A particular group of compounds suitable for oxidation with the present process are hydroxyalkylated, especially hydroxyethylated carbohydrates such as hydroxyethyl starch or hydroxyethyl inulin. These derivatives result in an alternative way for producing formylmethyl and carboxymethyl carbohydrates.

The oxidation of carbohydrates containing primary hydroxyl groups results in the corresponding carbohydrates containing aldehydes and/or carboxylic acids with intact ring systems. Examples include α-1,4-glucan-6-aldehydes, β-2,1-fructan-6-aldehydes and β-2,6-fructan-1-aldehydes, with the corresponding carboxylic acids. Where these products still contain the aldehydes, they are useful intermediates for functional carbohydrates wherein the aldehyde groups are further reacted with e.g. amine compounds and the like. They are also useful intermediates for crosslinked carbohydrates, in which the aldehyde groups are further reacted with e.g. diamine reagents.

EXAMPLES

Example 1

Potato starch (3.0 g, 18.5 mmol anhydroglucose units) was gelatinized in demi-water (200 ml) at 95° C. with effective mechanical stirring. 4-Acetamido-TEMPO (61 mg, 0.29 mmol) was added and dissolved. The solution was cooled on ice and the temperature was maintained ≦10° C. throughout the reaction. The reaction was initiated by the addition of Oxone® (11.38 g, 2 mol $HSO_5^-$/mol primary alcohol), which was added under mechanical stirring in small portions throughout the oxidation to minimize unwanted side reactions. After each addition of the acidic oxidant, pH was raised to 8.2 and then kept constant by the addition of 0.5 M NaOH using a pH stat apparatus. After completion of the reaction (8–10 hours), the remaining aldehyde intermediates were reduced to the starting alcohol using 150 mg of $NaBH_4$. After one hour, pH was adjusted to Ca. 6.0 with 0.5 M HCl and the reacted polysaccharides were precipitated in 2 volumes of ethanol, filtered off, and re-dissolved in 50 ml of water. Finally the materials were freeze-dried. The conversion of the primary hydroxyls to carboxyls was estimated by $^{13}C$ NMR to be 60 mol %.

Example 2

Methyl α-D-glucopyranoside (1.0 g, 5.1 mmol) and 4-acetamido-TEMPO (20 mg, 0.09 mmol) were dissolved in water (50 ml). The solution was cooled on ice and the temperature was maintained at ≦10° C. throughout the reaction. The reaction was initiated by the addition of Oxone® (3.17 g, 2 mol $HSO_5^-$/mol primary alcohol), which was added in small portions under mechanical stirring throughout the oxidation to minimize unwanted side reactions. After each addition of the acidic oxidant, pH was raised to 8.2 and then kept constant by the addition of 0.5 M NaOH using a pH stat apparatus. After completion of the reaction (6–8 hours), the remaining aldehyde intermediates were reduced to the starting alcohol using sodium borohydride (100 mg). After one hour, pH was adjusted to ca. 6.0 with 0.5 M MCl. Finally the materials were concentrated by rotary evaporation and freeze-dried. The conversion of the primary hydroxyls to carboxyls was estimated by $^{13}C$ NMR to be 62 mol %.

Example 3

Amylopectin (waxy starch maize) (3.0 g, 18.5 mmol anhydroglucose units) was gelatinized in demi-water (200 ml) at 95° C. with effective mechanical stirring. 4-Acetamido-TEMPO (61 mg, 0.29 mmol) was added and dissolved. The reaction was initiated by the addition of Oxone® (11.38 g, 2 mol $HSO_5^-$/mol primary alcohol), which was added under mechanical stirring in small portions throughout the oxidation to minimize unwanted side reactions. The reaction procedure was identical to that in Example 1. The conversion of the primary hydroxyls to carboxyls was estimated by $^{13}C$ NMR to be 58 mol %.

What is claimed is:

1. A halogen-free process of selectively oxidizing primary hydroxyl groups to carbaldehyde and/or carboxyl groups in a substrate having both primary and secondary hydroxyl groups comprising contacting the substrate with a cyclic nitroxyl compound in the presence of a co-oxidant in an aqueous medium, wherein the co-oxidant is a peroxosulfate, the oxidation is carried out at a temperature below 30° C. and at a pH below 9 and the oxidation is carried out in the absence of a metal catalyst; and wherein the substrate is a polysaccharide.

2. The process according to claim 1, wherein the co-oxidant is ($2KHSO_5 \cdot KHSO_4 \cdot K_2SO_4$).

3. The process according to claim 1, wherein the oxidation is carried out at a temperature between 0 and 25° C.

4. The process according to claim 1, wherein the oxidation is carried out at a pH between 6 and 9.

5. The process according to claim 1, wherein the co-oxidant is added gradually over the reaction period.

6. The process according to claim 1, wherein 0.001 to 0.1 mol of nitroxyl per mol of primary hydroxyl groups in the substrate is used.

7. The process according to claim 1, wherein the substrate is a glucan.

8. The process according to claim 7, wherein the substrate is selected from starch and cellulose.

9. The process according to claim 6, wherein 0.002 to 0.03 mol of nitroxyl per mol of primary hydroxyl groups in the substrate is used.

10. The process according to claim 1, wherein the oxidation is carried out at a temperature between 0 and 15° C.

11. A halogen-free process of selectively oxidizing primary hydroxyl groups to carbaldehyde and/or carboxyl groups in a polysaccharide having a chain length of at least 5 anhydroglycose units, comprising contacting the polysaccharide with a cyclic nitroxyl compound in the presence of a co-oxidant in an aqueous medium, wherein the co-oxidant is a peroxosulfate and the oxidation is carried out at a temperature below 30° C. and at a pH below 9.

12. The process according to claim 11, wherein the polysaccharide is a glucan.

13. A halogen-free process of selectively oxidizing primary hydroxyl groups to carbaldehyde and/or carboxyl groups in a substrate having both primary and secondary hydroxyl groups, comprising contacting the substrate with a cyclic nitroxyl compound in the presence of a co-oxidant in an aqueous medium, wherein the co-oxidant is a peroxosulfate and the oxidation is carried out at a temperature below 30° C. and at a pH below 9, and wherein the cyclic nitroxyl compound is 4-acetamido-TEMPO or 4-hydroxy-TEMPO or a derivative thereof; and wherein the substrate is a polysaccharide.

* * * * *